United States Patent [19]
Baer et al.

[11] Patent Number: 5,216,312
[45] Date of Patent: Jun. 1, 1993

[54] FLUID SENSING DEVICE HAVING REDUCED ATTENUATION OF SHEAR TRANSVERSE WAVES

[75] Inventors: Richard L. Baer; Curt Flory, both of Los Altos, Calif.

[73] Assignee: Hewlett-Packard Company, Palo Alto, Calif.

[21] Appl. No.: 843,779

[22] Filed: Feb. 28, 1992

[51] Int. Cl.⁵ .......................................... H01L 41/04
[52] U.S. Cl. ........................... 310/313 D; 310/313 R
[58] Field of Search ............... 310/311, 313 R, 313 D; 333/150–154

[56] References Cited

U.S. PATENT DOCUMENTS

| | | | |
|---|---|---|---|
| 4,814,658 | 3/1989 | Suthers et al. | 310/313 D |
| 4,837,476 | 6/1989 | Mochizuki | 310/313 R |
| 4,918,349 | 4/1990 | Shiba et al. | 310/313 C |
| 4,933,588 | 6/1990 | Greer | 310/313 D |
| 4,965,479 | 10/1990 | Elliott et al. | 310/313 D |
| 5,111,168 | 5/1992 | Panasik et al. | 310/313 D |

OTHER PUBLICATIONS

Wenzel et al., "Flexural Plate-wave Gravimetric Chemical Sensor", *Sensors and Actuators*, A21–A23 (1990), pp. 700–703.

Martin et al., "Characterization of SH Acoustic Plate Mode Liquid Sensors", *Sensors and Actuators*, 20 (1989), pp. 253–268.

D. F. Thompson, "Temperature Compensation of Microwave Acoustic Resonators", doctoral dissertation for Stanford University, Jun. 1986, Chapter III.

*Primary Examiner*—Steven L. Stephan
*Assistant Examiner*—Matthew Nguyen

[57] ABSTRACT

A fluid sensing device such as a Shear Transverse Wave device or a Love Wave device having a wave-trapping structure that provides tight surface trapping at transduction and sensing regions, but permitting a deeper penetration of wave energy at the interface of a seal with the wave-trapping structure. In the STW device, wave-trapping fingers are selectively varied in thickness, width or both to achieve the selective trapping. In an LW device, a wave-trapping plate is reduced in thickness at seal regions.

18 Claims, 3 Drawing Sheets

FLUID SENSING DEVICE HAVING REDUCED ATTENUATION OF SHEAR TRANSVERSE WAVES

DESCRIPTION

1. Technical Field

The present invention relates generally to Shear Transverse Wave and Love Wave devices and more particularly to increasing the sensitivity of a fluid sensor by reducing device-imposed attenuation of shear transverse waves.

2. Background Art

There are a number of types of piezoelectric devices that have been designed to perform electronic signal processing or to measure such variables as mass, pressure, viscosity and density. For example, a gravimetric sensor may be used to measure the concentration of a selected class of compounds in a chemical solution into which the sensor is immersed. In addition to use with liquids, piezoelectric sensors may be utilized with gases.

As used herein, such piezoelectric devices are broadly classified as "bulk wave devices," "plate wave devices" and "surface wave devices." A bulk wave device is one in which an acoustic wave tends to propagate and extend throughout the full thickness of a piezoelectric substrate. A plate wave device is one in which acoustic energy is confined by reflection from the top and bottom surfaces of a plate. A surface wave device is one in which acoustic energy is confined in a vertical direction (i.e. a direction perpendicular to a substrate surface) in a region adjacent to the substrate surface.

Each of the three classes can be subclassified by the orientation of the acoustic wave motion with regard to the substrate surface of the device. The three types of wave motion are: (1) longitudinal wave motion in which material displacement is in a direction parallel to the direction of propaqation of the wave: (2) shear vertical wave motion in which material displacement is in a direction perpendicular to both the substrate surface and the direction of wave propagation; and (3) shear transverse, or shear horizontal, wave motion in which material displacement is perpendicular to the direction of propagation and parallel to the substrate surface.

A "Surface Acoustic Wave" (SAW) device is one type of surface wave device. This type is also known as a "Rayleigh Wave" (RW) device and utilizes waves that are predominantly shear vertical, with the energy localized within an acoustic wave length of the substrate surface. While this type operates efficiently in many applications, the shear vertical wave motion may adversely affect performance when the SAW device is used as a sensor in a liquid. The shear vertical component of wave motion presses against the fluid under test. If the surface wave velocity is greater than the fluid compressional wave velocity, energy will be radiated into the fluid. Because the energy of the surface wave leaks away into the fluid, the fluid compressional waves are called "leaky waves." The attenuation resulting from leaky-wave radiation causes an unacceptable amount of insertion loss, rendering the device inoperable.

A "Flexural Plate Wave" (FPW) device also utilizes shear vertical wave motion. An FPW sensor has a thin plate that is fabricated by using conventional semiconductor fabrication techniques. An FPW chemical sensor is described by Wenzel et al. in "Flexural Platewave Gravimetric Chemical Sensor," *Sensors and Actuators*, A21-A23 (1990), pages 700-703. A region for the flow of a vapor or a liquid is etched into a silicon substrate and an ultrasonic delay line consisting of a composite plate of low-stress silicon nitride, aluminum and zinc oxide is used as the plate for the top-to-bottom reflection of wave energy. The FPW sensor has the advantage of exhibiting an acoustic velocity that is less than the acoustic velocity of most liquids, thereby avoiding the "leaking away" of wave energy into the liquid. However, the FPW sensor is overly sensitive to small changes in liquid density, pressure and temperature. Moreover, the sensor is relatively fragile, since the plate is extremely thin.

Shear transverse wave motion is the preferred orientation of acoustic wave motion within a fluid sensor. Shear transverse waves are not affected by the same leaky wave mechanism, since the material displacement at the fluid/substrate interface is parallel to the substrate surface and is not pressed against the fluid. The absence of the surface-normal component of material displacement allows the shear transverse waves to propagate without unacceptable amounts of wave energy dissipation into the fluid under test.

An "Acoustic Plate Mode" (APM) liquid sensor using shear transverse waves is described by Martin et al. in "Characterization of SH Acoustic Plate Mode Liquid Sensors," *Sensors and Actuators*, 20 (1989), pages 253-268. APM sensors are less susceptible to leaky-wave attenuation, but are typically less sensitive than SAW devices.

A "Surface Skimming Bulk Wave" (SSBW) device utilizes shear transverse wave motion. The Surface Skimming Bulk Wave type is also referred to as a "Shallow Bulk Acoustic Wave" (SBAW) device. Propagation occurs by way of bulk mode, in which the waves graze the surface and diffract into the piezoelectric substrate. Bulk propagating modes have higher velocities than Rayleigh waves, but are more susceptible to losses due to inefficient coupling of power to and from the substrate. Moreover, diffraction losses are significant.

"Love Wave" (LW) devices differ from an SSBW by the inclusion of a plate that functions as a surface trapping structure to trap the wave energy proximate to the surface of the piezoelectric substrate. Addition of the plate provides mass loading and causes piezoelectric shorting which slows down the skimming bulk shear wave, thereby creating a decay of the wave function into the depth of the substrate. The material selected in fabricating the plate is conventionally one having a lower acoustic shear wave velocity than the piezoelectric substrate, so that the plate slows the shear transverse wave even further.

A "Surface Transverse Wave" (STW) device also utilizes shear horizontal wave motion. The STW device differs from the Love Wave device only by the replacement of the wave-trapping plate with surface grooves or with a raised grating of fingers. The grating of fingers provides stronger surface trapping than the plate. Thus, high velocity bulk modes are further trapped near the surface of the substrate, allowing an even greater coupling of power through more efficient transduction.

Typically, an LW sensor or an STW sensor includes a transmitting interdigital transducer having an array of interleaved electrode fingers to launch shear transverse waves along a sensing region of a piezoelectric substrate in response to an electrical signal. On the opposite side of the sensing region is a receiving interdigital transducer, which detects the waves and generates a corresponding output signal. In its simplest form, such sensors act as highly sensitive detectors of changes in surface mass, responding to accumulated mass per unit area. More sophistication is achieved by coating the surface of the piezoelectric substrate with a chemically reactive layer that preferentially reacts with a constituent within the fluid under test. Depending upon the concentration of the constituent within the fluid, the mass of the chemically reactive layer will fluctuate. The change in mass of the layer causes a corresponding change in the phase delay or acoustic shear wave velocity of the sensor. Thus, the sensor may be dedicated to detection of a specific constituent, such as a particular antibody within a solution.

One concern in the use of an LW sensor or an STW sensor is the effect of the fluid under test on the transmitting and receiving interdigital transducers. Typically, the electrode fingers of each of the transducers are interleaved metallic members. Depending upon the fluid under test, the fluid may cause corrosion of the electrode fingers. Moreover, the fluid may electrically short the electrode fingers together. Therefore, preferably the fluid is sealed within the sensing region of the sensor and prevented from reaching the interdigital transducers. For example, a flow cell may be mounted to the surface of the piezoelectric substrate and a compliant gasket may be sandwiched between the flow cell and the substrate surface.

Sealing the fluid flow from the interdigital transducers solves the problems of electrical shorting and premature corrosion, but creates other problems. Firstly, the compliant gasket is another source of leaky-wave attenuation. Wave energy leaks away from the sensor substrate into the compliant gasket in the form of shear waves. Secondly, in addition to leaky-wave attenuation, other mechanisms cause the gasket to reflect or absorb wave energy, leaving a smaller fraction of wave energy propagating from the transmitting interdigital transducer to the receiving interdigital transducer. The wave attenuation increases with the length and the mechanical rigidity of the gasket or other sealing member. Consequently, the choice of the means for providing a fluid-tight seal represents a compromise between attenuation and fluid sealing considerations. That is, the compromise is between the sensitivity of the sensor and the reliability of the seal.

It is an object of the present invention to improve the sensitivity and performance of fluid sensors that utilize shear transverse wave propagation along a substrate having a fluid seal coupled to the surface of the substrate.

SUMMARY OF THE INVENTION

The above object has been met by a fluid sensing device in which the trapping of shear transverse wave energy is selectively relaxed and tightened to reduce the susceptibility of the device to the attenuation of wave energy by a seal. The relaxation of trapping allows a greater penetration depth of wave energy at the seal regions of a piezoelectric substrate. Within a sensing region of the piezoelectric substrate, the surface transverse waves are more tightly trapped to maximize the sensitivity of the sensor. Preferably, the tight trapping of energy is also provided at transmitting and receiving interdigital transducers in order to efficiently couple power into and out of the piezoelectric substrate.

In a first embodiment, the fluid sensing device is a Surface Transverse Wave device having an array of grooves or fingers that function as a wave-trapping structure. The thickness of the fingers or grooves may be selectively varied. A thick finger yields tight trapping that allows efficient electromechanical coupling between the piezoelectric substrate and the transducers and draws the wave energy to the substrate surface at the sensing region to maximize the sensitivity of the sensor. Thus, the wave-trapping structure should be thickest at areas near the interdigital transducers and at the sensing region. The fingers or grooves are tapered with approach to and departure from seal regions associated with contact with a gasket or other means of providing a fluid-tight seal. The tapering allows increased wave penetration depth at the seal regions, so that the interface of the piezoelectric substrate with the gasket does not provide a highly efficient mechanism for attenuation. Loosely trapping the wave energy at the seal regions reduces the susceptibility of the sensor to device-induced attenuation.

An alternative tapering mechanism for selectively relaxing and tightening trapping involves the width-to-spacing ratio of the fingers or grooves of the first embodiment. Tapering the width-to-spacing ratio is preferred to a tapering of the height, since conventional fabrication techniques do not readily allow highly controlled variations in thickness. It has been discovered that changes in width for a given center-to-center distance, i.e. periodicity, of fingers or grooves will affect trapping. An array of wide fingers more tightly traps wave energy to the substrate surface. In the same manner as the tapering of the height, the width-to-spacing ratio of fingers is gradually decreased with approach to seal regions and gradually increased with departure from the seal regions. A third alternative is to combine the tapering of height and width to maximize trapping selectivity. A fourth alternative is to selectively vary the periodicity. However, this is the least desirable of the alternatives, since the period is preferably fixed in order to restrict the effects of Bragg scattering to a small range of frequencies.

In a second embodiment, the sensing device is a Love Wave device. The thickness of a wave-trapping plate is selectively varied in the same manner described with reference to varying the height of fingers of an STW device. The thickness of the wave-trapping plate is at a minimum at seal regions and is at a maximum in a sensing region and at areas close to the interdigital transducers.

An advantage of the present invention is that the selective trapping permits highly sensitive measurements by an STW or LW device, while isolating the interdigital transducers from the fluid. In the prior art, attenuation of wave energy was minimized by carefully selecting the placement, the composition and the dimensions of a gasket or other seal member. Another advantage of the present invention is that the selective trapping eases the restrictions on the nature, placement and dimensions of the gasket. Performance is enhanced and, simultaneously, manufacturing costs may be reduced.

BEST MODE FOR CARRYING OUT THE INVENTION

Figure 1:
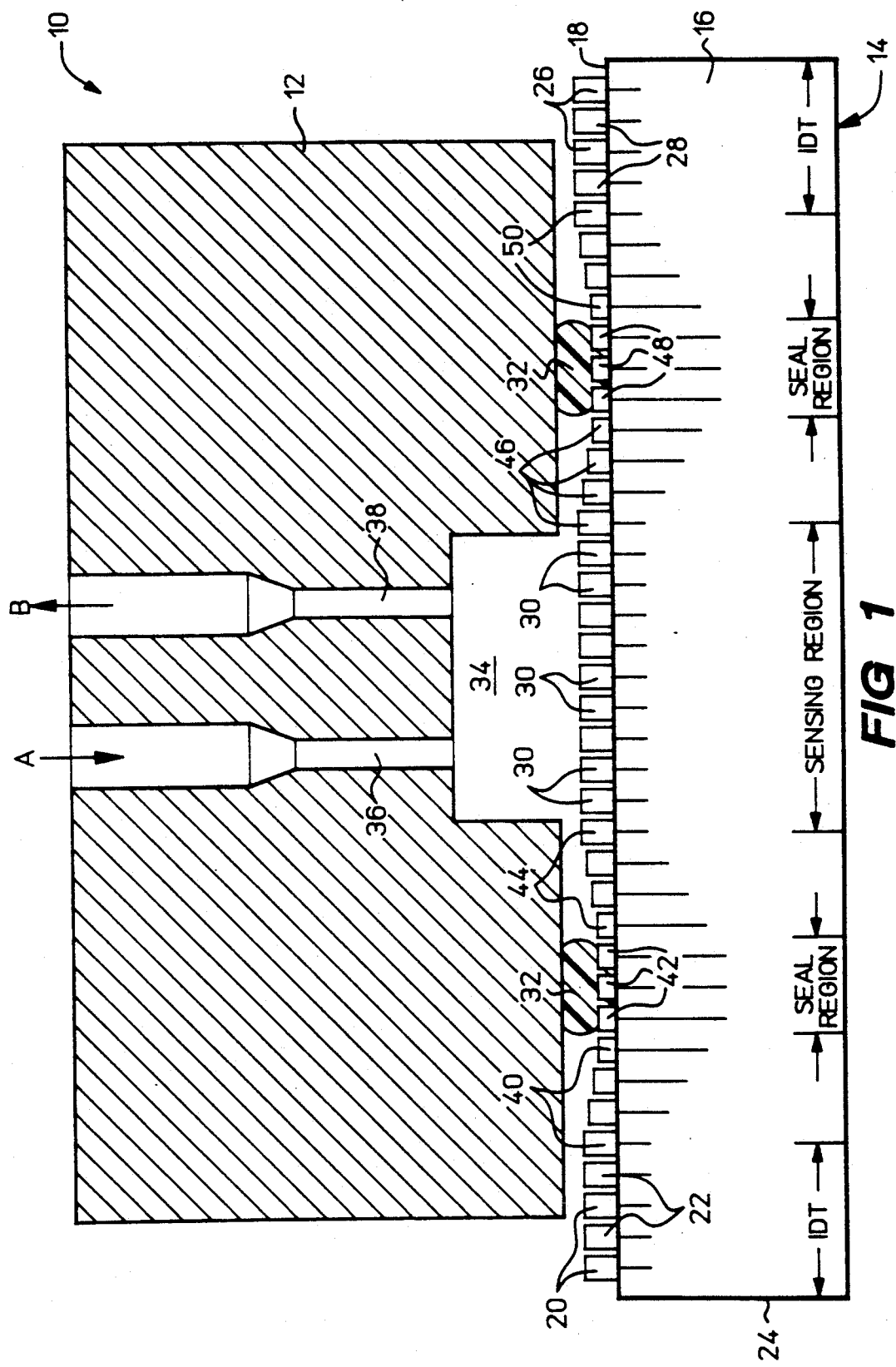
FIG. 1 is a side view of a first embodiment of a Surface Transverse Wave device utilized as a fluid sensor in accord with the present invention.

With reference to FIG. 1, a fluid sensor 10 includes a flow cell 12 and a Surface Transverse Wave (STW) device 14. The STW device includes a piezoelectric substrate 16 having a substrate surface 18 for the propagation of shear transverse, or shear horizontal, wave motion in which displacement of piezoelectric material is perpendicular to the direction of propagation and parallel to the substrate surface. The piezoelectric material may be quartz, $LiTaO_3$, $LiNbO_3$, or any other material known for use with STW devices. The piezoelectric substrate 16 is cut to couple energy from a transmitting interdigital transducer having electrode fingers 20 and 22 into shear transverse waves. The choice of substrate material and the cut are also selected to enable trapping of wave energy at the substrate surface 18.

Alternating electrode fingers 20 of the transmitting interdigital transducer are electrically connected and are interleaved with the electrode fingers 22. The electrode fingers are made of a conductive material, such as aluminum, which is deposited and photolithographically patterned on the substrate surface 18. The deposition of the conductive material which forms the electrode fingers 20 and 22, as well as other fingers to be described below, is provided by conventional methods, such as evaporation or sputter deposition. The electrode fingers have a typical thickness within the range of 0.01 micron to 1.0 micron. The width of an electrode finger may be within the range of 1 micron to 100 microns. An applied voltage difference between the electrode fingers 20 and the electrode fingers 22 produces an electric field that interacts electromechanically with the piezoelectric substrate 16 to launch surface transverse waves along a sensing region of the piezoelectric substrate. A grating of fingers, not shown, may be fabricated between the transmitting interdigital transducer and a first edge 24 of the piezoelectric substrate 16.

An output interdigital transducer having electrode fingers 26 and 28 is formed near the end of the substrate surface 1 opposite to the electrode fingers 20 and 22 of the transmitting interdigital transducer. In operation, an alternating voltage is supplied to the transmitting interdigital transducer to provide an electric field between the electrode fingers 20 and 22. A stress field is generated by the electromechanical action of the piezoelectric substrate 16. Because of the particular crystalline structure of the piezoelectric substrate, this stress field generates shear transverse waves at a designed frequency. The shear transverse waves propagate toward the electrode fingers 26 and 28 of the output interdigital transducer and create an electric field between electrode fingers 26 and electrode fingers 28, producing an output signal.

Shear transverse waves have an inherent characteristic of diffracting into the bulk of the piezoelectric substrate 16 as the waves propagate from the transmitting interdigital transducer to the receiving interdigital transducer. However, it is known that periodic perturbations formed at the substrate surface will function to trap wave energy closer to the substrate surface. The periodic perturbations may be formed by cutting grooves into the piezoelectric substrate 16. Alternatively, an array of wave-trapping fingers may be fabricated in the same photolithographical steps used to deposit the electrode fingers 20, 22, 26 and 28 of the transducers. Wave-trapping fingers slow the shear transverse waves, thereby creating a decay of the wave function into the depth of the piezoelectric substrate 16. This "slowing effect" that creates the trapping is due to the multiple reflections from the individual fingers. Typically, the fingers are photolithographically patterned from a layer of metal, such as aluminum. Because metals are particularly dense, metallic fingers are thinner than functionally comparable wave-trapping fingers of other materials. In addition, metallic fingers can short out the piezoelectric substrate 16 at its upper surface, thereby reducing the stiffness of the substrate at its upper surface. This provides increased trapping of shear transverse waves. However, other materials may be utilized.

In operation, at least those wave-trapping fingers 30 within the center of the piezoelectric substrate 16 are formed from a number of layers of material. As described above, the first material was preferably a metal that can short out the piezoelectric substrate at its upper surface to enhance trapping of shear transverse waves. A second layer is an attachment layer that may be deposited by sputtering or by evaporation. For example, a layer having a thickness within the order of 10 to 1000 angstroms may be formed to protect the metallic layer of the fingers 30 from attack by chemicals. This protective layer may also cover the substrate surface 18 where the surface is exposed by spacings between the wave-trapping fingers 30. For embodiments that are to serve as chemical sensors, a chemically reactive layer is then deposited. The chemically reactive layer is chosen to preferentially react with a constituent of a fluid under test. Silicon dioxide may be used, since a large amount of literature is available regarding binding various chemically selective compounds to silicon dioxide. Other layers may also be used. For example, a uniform grounded metallic layer may be formed either above or below the fingers 30 to shield propagating shear transverse waves from the conductivity of the liquid or gas under test.

Mounted to the STW device 14 is the flow cell 12. The manner of coupling the flow cell and the STW device is not critical. However, an important concern is the effect of a fluid under test on the electrode fingers 20, 22, 26 and 28 of the opposed interdigital transducers. The fluid may cause corrosion of the electrode fingers, or may electrically short electrode fingers 20 of the transmitting interdigital transducer to the other electrode fingers 22 of the same transducer. To prevent corrosion, electrical shorting and any other adverse effect of the fluid on outside structure, and to restrict the flow of the fluid to a controlled area, a gasket 32 is used to seal a flow region 34 of the cell 12. As indicated by arrow A, the fluid under test is introduced through an input passageway 36. Typically, the fluid is a liquid having a constituent that is of interest. The liquid then exits through an output passageway 38, as indicated by arrow B.

The flow cell 12 is not critical to the present invention. The surface transverse wave device 14 may be immersed into a fluid under test. In this case, the electrode fingers 20, 22, 26 and 28 of the interdigital transducers may be sealed within separate enclosures to prevent corrosion and electrical shorting. Regardless, a problem with sealing the transducers from the flow of fluid is selecting the optimal placement of the seal and selecting the material for making the seal. The seal, such as the gasket 32 of FIG. 1, will absorb shear transverse wave energy from the piezoelectric substrate 16. This attenuation of energy reduces the sensitivity of the fluid sensor 10.

The present invention significantly reduces this structure-induced attenuation by a seal member. The height of the wave-trapping mechanism is selectively varied to provide tight trapping at the sensing region of fingers 30 and tight trapping at the electrode fingers 20, 22, 26 and 28 of the transducers, but to permit diffraction of wave energy into the piezoelectric substrate 16 with approach to the area of the substrate surface 18 coupled to the gasket 32. "Tight trapping" is referred to herein as a trapping of shear transverse wave energy to a maximum depth of three wavelengths of the propagating waves. The series of vertical lines extending downwardly from the substrate surface 18 into the piezoelectric substrate 16 is provided as a graphical illustration of wave penetration depth, although the bars are not intended to be proportional representations of penetration. Typically, the number of wave-trapping fingers between the interdigital transducers greatly exceeds the number shown in FIG. 1.

The wave-trapping fingers, between the electrode fingers 20, 22, 26 and 28 slow the propagating shear transverse waves. The height, or thickness, of the fingers affect the penetration of the shear transverse waves. Wave-trapping fingers 40 between the transmitting interdigital transducer and the gasket 32 are tapered to allow a greater wave penetration with approach to the gasket 32. As the height is decreased, the wave function decays further into the interior of the piezoelectric substrate 16. For a given finger grating periodicity (p=0.475 times the wavelength (λ) of STWs) at a given ratio of finger width-to-p (r=0.5), the following results were computationally determined for different uniform heights within a grating:

CASE 1—Where h=0, the STW power penetrates through the entire substrate, i.e., there is no surface trapping;

CASE 2—Where h=0.01 p, the STW power decays to 25% of its substrate surface value at a depth of 6λ;

CASE 3—Where h=0.02 p, the STW power decays to 25% of its substrate surface value at a depth of 4λ; and CASE 4—Where h=0.03 p, the STW wavelength decays to 25% of its substrate surface value at 3λ.

The change in the height of the wave-trapping fingers 40 should be a gradual taper. Abrupt transitions create reflection-inducing discontinuities that affect the performance of the fluid sensor 10. The wave-trapping fingers 40 close to the transmitting interdigital transducer should have a height generally equivalent to that of the electrode fingers 20 and 22. This ensures an efficient coupling of power from the transducer to the piezoelectric substrate 16. The wave-trapping fingers taper to the height of fingers 42 within the seal region of the piezoelectric substrate. As the wave energy decays into the substrate, the wave becomes less sensitive to surface conditions such as contact with the gasket 32. Consequently, by relaxing the trapping of wave energy, attenuation caused by the gasket is significantly reduced.

In the same manner that the wave-trapping fingers 40 relax the trapping of wave energy with approach to the gasket 32, wave-trapping fingers 44 between the seal region and the fingers 30 of the sensing region gradually increase in height to again tightly trap the wave energy. Thus, the STW device 14 is most sensitive to surface conditions in that region where high sensitivity is desirable.

Wave-trapping fingers 46 then allow a second gradual decay of the waves with approach to the gasket 32. Again, the increased penetration causes the waves to be less susceptible to the contact of the gasket with the substrate surface 18. A last series of tapering wave-trapping fingers 50 draws the energy to the surface for efficient decoupling of the energy by the electrode fingers 26 and 28 of the output interdigital transducer.

One problem with the embodiment of FIG. 1 involves fabrication of the STW device 14. Preferably the wave-trapping fingers 30 and 40-50 would be formed in a single fabrication step. This would require controlling the rate of material deposition as a function of position on the substrate surface 18. For example, in deposition by evaporation, a pair of wires could be suspense in spaced-apart relation from the substrate 16 directly over the seal regions of the substrate. Each wire would function as a shadow mask for the seal region. Evaporated metal would then be shadowed and a gradual variation of metal height would occur.

An alternative would be to employ a number of steps to selectively build the fingers 30 and 40-50. A first deposition would form the metal fingers at a uniform height, whereafter selected fingers, such as the wave-trapping fingers 30 within the sensing region would receive a second layer of the same metallic material. The number of steps would then depend upon the number of thicknesses of fingers. For example, concentrating on the fingers 40 between the transmitting interdigital transducer and the gasket 32, four steps would be required in forming these four fingers of different heights.

Figure 2:
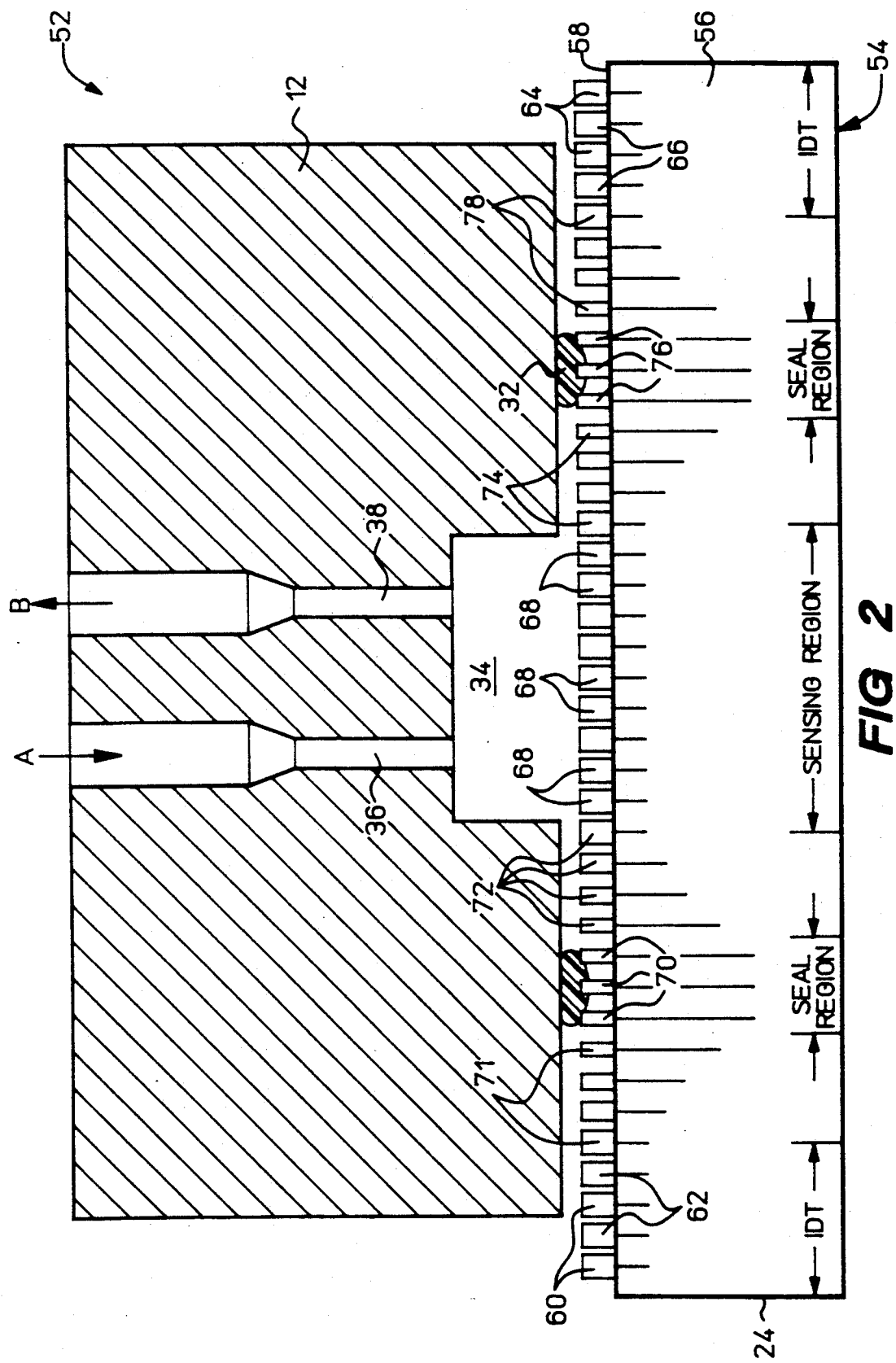
FIG. 2 is a side view of a second embodiment of a Surface Transverse Wave device in accord with the present invention.

FIG. 2 illustrates a fluid sensor 52 which can be more easily fabricated. For this reason, FIG. 2 is an embodiment that is preferred over the one described above and illustrated in FIG. 1. The fluid sensor 52 includes an identical flow cell 12 and includes a surface transverse wave device 54. A piezoelectric substrate 56 having a substrate surface 58 is functionally identical to the one described above, but the selective tightening and relaxing of wave trapping is accomplished by varying the width of wave-trapping fingers. Electrode fingers 60, 62, 64 and 66 of the interdigital transducers and wave-trapping fingers 68 on a substrate surface 58 are dimensionally and compositionally identical to those of the first embodiment. To maximize performance, the period of the fingers is fixed across the substrate surface. However, the widths of adjacent fingers 71 disposed between the transmitting interdigital transducer and the gasket 3 gradually decrease to allow greater penetration of wave energy into the substrate 56, as shown graphically by the bars extending downwardly from the fingers. The decay of wave energy renders the device 54 less susceptible to attenuation of energy into the gasket 32. The width of the fingers is minimized at contact of the gasket with wave-trapping fingers 70. A variable grating of fingers 72 again draws the waves toward the surface with departure from the gasket. The waves are tightly trapped by wide wave-trapping fingers 68 within the sensing region.

Narrowing wave-trapping fingers 74 again allow decay with approach to the portion of the gasket 32 that protects the electrode fingers 64 and 66 of the receiving interdigital transducer. Fingers 76 at the gasket preferably prevent decay to the bottom surface of the piezoelectric substrate 56. A last array of gradually widening wave-trapping fingers 78 is used to draw the wave energy to the substrate surface 58 for decoupling of the energy by the output interdigital transducer.

For a given grating periodicity ($p = 0.475 \lambda$) and a given grating height ($h = 0.01 p$), the following results were computationally determined for different ratios (r) of finger width-to-p:

CASE 5—Where $r = 0.4$, the STW power decays to 25% of its substrate surface value at a depth of $7\lambda$;

CASE 6—Where $r = 0.5$, the STW power decays to 25% of its substrate surface value at a depth of $6\lambda$;

CASE 7—Where $r = 0.6$, the STW power decays to 25% of its substrate surface value at a depth of $4\lambda$;

CASE 8—Where $r = 0.8$, the STW power decays to 25% of its substrate surface value at a depth of $3\lambda$; and CASE 9—Where $r = 1.0$, the STW power decays to 25% of its substrate surface value at a depth of $2\lambda$.

Alternatively, it would be possible to combine the varying thickness of FIG. 1 and the varying width of FIG. 2 to provide a fluid sensor that would allow greater control of gradual transitions in wave penetration. Disregarding difficulties in fabrication, this would be a preferred structure, since gradual variations avoid reflections that occur when waves encounter abrupt discontinuities in structural aspects such as thickness and width.

A less desirable method of controlling the depth of penetration is to vary the periodicity of the wave-trapping fingers of an STW device. An increase in the period of the fingers increases the surface trapping, while a decrease allows greater penetration. However, the period is preferably fixed, so as to restrict the effects of Bragg scattering to a small range of frequencies.

Figure 3:
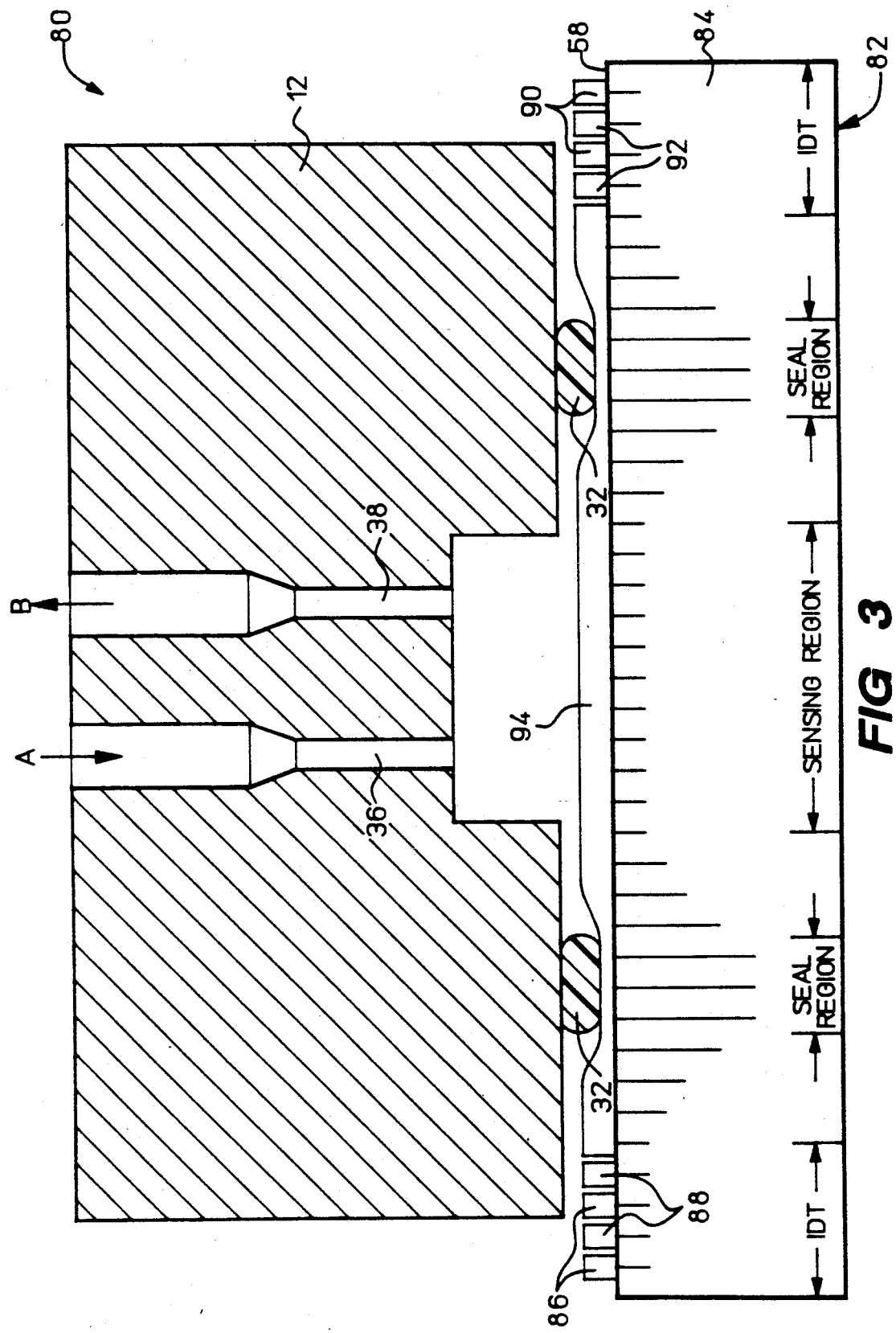
FIG. 3 is a side view of a Love Wave device for use as a fluid sensor in accord with the present invention.

Another embodiment of the present invention is illustrated in FIG. 3. A fluid sensor 80 includes a flow cell 12 that is identical to the one described above, but the flow cell is coupled to a Love Wave (LW) device 82. A piezoelectric substrate 84 has electrode fingers 86 and 88 that form a transmitting interdigital transducer and includes electrode fingers 90 and 92 of an input interdigital transducer.

Between the electrode fingers is a wave-trapping plate 94. While the plate 94 is known to be less efficient at trapping wave energy than the periodic perturbations of an STW device, the plate slows the shear transverse waves to restrict the tendency of such waves to diffract into the entirety of the piezoelectric substrate 84. As in the embodiments described above, the wave-trapping structure is preferably made of metal, but this is not critical. Any material which has an acoustic velocity less than that of the piezoelectric substrate may be used. Typically, the plate 94 is a multi-layered structure having a reactive layer that is chemically reactive to a constituent of a fluid under test.

The wave-trapping plate 94 is varied in thickness to selectively relax and tighten trapping of wave energy. A reduced thickness at the interface of the plate with the gasket 32 allows sufficient penetration to render the LW device 82 less susceptible to attenuation resulting from this gasket/plate contact. The bars extending downwardly from a plate into the piezoelectric substrate 84 are employed to illustrate changes in penetration depth.

In all of the embodiments described above, shear transverse wave energy is only lightly coupled to the piezoelectric surface at the interface of the piezoelectric substrate with a seal. Thus, the importance of the choice of materials in constructing the seal is reduced somewhat. In the prior art, the seal had to be sufficiently compliant to prevent unacceptable levels of attenuation. The present invention allows a manufacturer to select between a greater number of materials and to place greater emphasis on selecting a material that is chemically resistant to a fluid under test and that is more rigid so as to provide a more reliable seal.

We claim:

1. A sensing device for use in testing with fluids comprising,
   a substrate having transducer means for propagating shear transverse waves along a length of a sensing region of said substrate, said substrate having a substrate surface,
   a body mounted to said substrate at said substrate surface for coupling a fluid under test to said sensing region, said body having sealing means disposed between said transducer means and said sensing region for providing a fluid-tight seal, and
   wave-trapping means on said substrate surface for controlling a depth of penetration of shear transverse wave energy into said substrate, said wave-trapping means having a dimensional configuration to allow a deeper penetration of wave energy at said sealing means than at said sensing region and to tightly trap shear transverse waves propagating along said sensing region.

2. The device of claim 1 wherein said wave-trapping means is a grating of fingers, each finger having a width substantially parallel to said length of said sensing region, the widths of fingers disposed on said sensing region being greater than the widths of fingers disposed between said sensing region and said transducer means, thereby allowing said deeper penetration of wave energy at said sealing means.

3. The device of claim 2 wherein adjacent fingers have gradual variations of widths both with approach and with departure from said sealing means.

4. The device of claim 1 wherein said wave-trapping means is a grating of fingers, each finger having a height from said substrate surface, the heights of fingers disposed on said sensing region being greater than the heights of fingers disposed between said sensing region and said transducer means, thereby allowing said deeper penetration of wave energy at said sealing means.

5. The device of claim 4 wherein adjacent fingers have gradual variations of thicknesses both with approach and with departure from said sealing means.

6. The device of claim 1 wherein said wave-trapping means is a plate disposed on said substrate surface, said plate having a varying height from said substrate surface, the height being greater at said sensing region than between said sensing region and said transducer means, thereby allowing said deeper penetration of wave energy at said sealing means.

7. The device of claim 1 wherein said transducer means includes a transmitting interdigital transducer for launching shear transverse waves and includes an output interdigital transducer for receiving waves, said transmitting interdigital transducer and said output interdigital transducer being on opposite sides of said sensing region, said sealing means being a gasket between said sensing region and each of said transmitting and output interdigital transducers.

8. A Surface Transverse Wave device for use in testing with fluids comprising, piezoelectric means for propagating shear transverse waves, said piezoelectric means having a substrate surface having a sensing region and having input and output transducers spaced apart from said sensing region by seal regions, said piezoelectric means having a grating of wave-trapping perturbations on said substrate surface, each wave-trapping perturbation having a width and a height from said substrate surface, at least one of said widths and said heights being varied among adjacent wave-trapping perturbations within said seal regions, means coupled to said substrate surface for applying a fluid under test to said sensing region, and means for sealing said fluid under test from contact with said input and output transducers, said sealing means contacting said piezoelectric means at said seal regions, wherein said at least one of said widths and heights of wave-trapping perturbations is dimensionally reduced at said seal regions relative to said sensing region to provide reduced trapping at said seal regions.

9. The device of claim 8 wherein said widths of said wave-trapping perturbations are tapered with approach and with departure from said sealing means, said widths being at a minimum at said sealing means.

10. The device of claim 8 wherein said heights of said wave-trapping perturbations are tapered with approach and with departure from said sealing means, said heights being at a minimum at said sealing means.

11. The device of claim 8 wherein said means for applying a fluid is a cell body having an inlet and an outlet for the flow of liquid along said piezoelectric means.

12. The device of claim 8 wherein said sealing means is a gasket.

13. The device of claim 12 wherein said gasket is a silicone rubber member.

14. A Love Wave device for use in testing with fluids comprising, piezoelectric means for propagating shear transverse waves, said piezoelectric means having a substrate surface having a sensing region and having input and output transducers on opposed sides of said sensing region, a wave-trapping plate positioned on said substrate surface between said input and output transducers, means coupled to said piezoelectric means for applying a fluid under test to said sensing region, and means for sealing flow of said fluid under test from said input and output transducers, said sealing means coupled to seal regions of said wave-trapping plate, wherein said wave-trapping plate varies in height, having a minimum height at said seal regions.

15. The device of claim 14 wherein said wave-trapping plate has a maximum height at said sensing region of said substrate surface, said height tapering gradually to said minimum height with approach to said seal regions.

16. The device of claim 14 wherein said height of said wave-trapping plate increases in opposite directions with departure from said seal regions.

17. The device of claim 14 wherein said wave-trapping plate is metallic.

18. The device of claim 14 wherein said means for applying a fluid includes a cell having an inlet and an outlet for the flow of a liquid along said sensing region.

* * * * *